(12) United States Patent
Kuroda

(10) Patent No.: US 8,778,686 B2
(45) Date of Patent: Jul. 15, 2014

(54) AUTOMATIC ANALYZER AND DISPENSING METHOD THEREOF

(75) Inventor: Akihisa Kuroda, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 284 days.

(21) Appl. No.: 12/345,112

(22) Filed: Dec. 29, 2008

(65) Prior Publication Data

US 2009/0169432 A1 Jul. 2, 2009

(30) Foreign Application Priority Data

Dec. 28, 2007 (JP) ................................. 2007-341073

(51) Int. Cl.
*G01N 35/10* (2006.01)
(52) U.S. Cl.
USPC .................................. 436/55; 436/49; 436/50
(58) Field of Classification Search
CPC ............................................. G01N 2035/0491
USPC .................................. 436/49, 55, 50; 422/106
See application file for complete search history.

(56) References Cited

U.S. PATENT DOCUMENTS

| 2005/0242117 A1 | 11/2005 | Yoshida et al. | |
| 2005/0282291 A1* | 12/2005 | Pankratz et al. | ............ 436/180 |

FOREIGN PATENT DOCUMENTS

| CN | 1651921 A | 8/2005 |
| JP | 5-40123 A | 2/1993 |
| JP | 6-43174 A | 2/1994 |
| JP | 2000-46843 A | 2/2000 |
| JP | 2000-171470 A | 6/2000 |
| JP | 2006-10484 A | 1/2006 |
| JP | 2007-316012 A | 12/2007 |
| JP | 2007-316013 A | 12/2007 |
| JP | 2007-322317 A | 12/2007 |

OTHER PUBLICATIONS

Chinese Office Action dated Aug. 13, 2012, issued in corresponding Chinese patent application No. 200810188144.9, w/ English translation.
Japanese Office Action dated Nov. 20, 2012, issued in Japanese Patent Application No. 2008-306561.
Japanese Office Action dated Sep. 25, 2013, issued in Japanese Patent Application No. 2008-306561.

\* cited by examiner

*Primary Examiner* — Natalia Levkovich
(74) *Attorney, Agent, or Firm* — Westerman, Hattori, Daniels & Adrian, LLP

(57) ABSTRACT

Provided are an automatic analyzer which moves a dispensing apparatus having a dispensing probe, or a vessel by a driving mechanism to dispense plural liquids into the vessel via the dispensing probe, and measures and analyzes optical characteristic of a reaction liquid in which each of the dispensed liquids is reacted, and a dispensing method thereof. The automatic analyzer includes a drive controlling unit which controls the driving mechanism so that the liquid surface of the liquid and a distal end of the dispensing probe are moved relatively to each other in a vertical direction, and, when the liquids including precipitated substance are to be dispensed, the dispensing probe sucks in the liquids from plural different positions along the vertical direction.

6 Claims, 5 Drawing Sheets

AUTOMATIC ANALYZER AND DISPENSING METHOD THEREOF

BACKGROUND OF THE INVENTION

1. Field of the Invention

The present invention relates to an automatic analyzer and a dispensing method thereof.

2. Description of the Related Art

Conventionally, a dispensing apparatus for dispensing a specimen and a reagent, which is included in an automatic analyzer, dispenses a specimen whose component is precipitated over time after harvested, for example, blood (whole blood) to analyze components of red blood cells, i.e., hemoglobin A1c (HbA1c). In this case, the dispensing apparatus detects a height of a liquid surface of the blood inside a specimen vessel, and inserts a distal end of dispensing probe into a predetermined certain position substantially at a middle of the blood, and the dispensing probe is stopped there to suck in the component of blood with a sucking operation, and dispensing the component of blood into a reaction vessel (e.g., see Japanese Patent No. 3763212).

SUMMARY OF THE INVENTION

An automatic analyzer according to an aspect of the present invention includes a dispensing apparatus that includes a dispensing probe; a vessel into which plural kinds of liquids are dispensed with the dispensing probe; a driving unit that moves the dispensing apparatus or the vessel; a drive controlling unit that controls the driving unit so that a distal end of the dispensing probe and a liquid surface of the liquid are moved relatively to each other in a vertical direction, and, when liquids including precipitated substance are dispensed, the dispensing probe sucks in the liquids from plural positions which differ from each other along the vertical direction; and an analyzing unit that measures and analyzes optical characteristic of a reaction liquid that the dispensed liquids have been reacted.

A dispensing method according to another aspect of the present invention is for dispensing liquids including precipitated substance contained in a vessel with a dispensing probe, and includes dispensing the liquid including the precipitated substance by sucking in from plural positions which differ from each other in a vertical direction.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
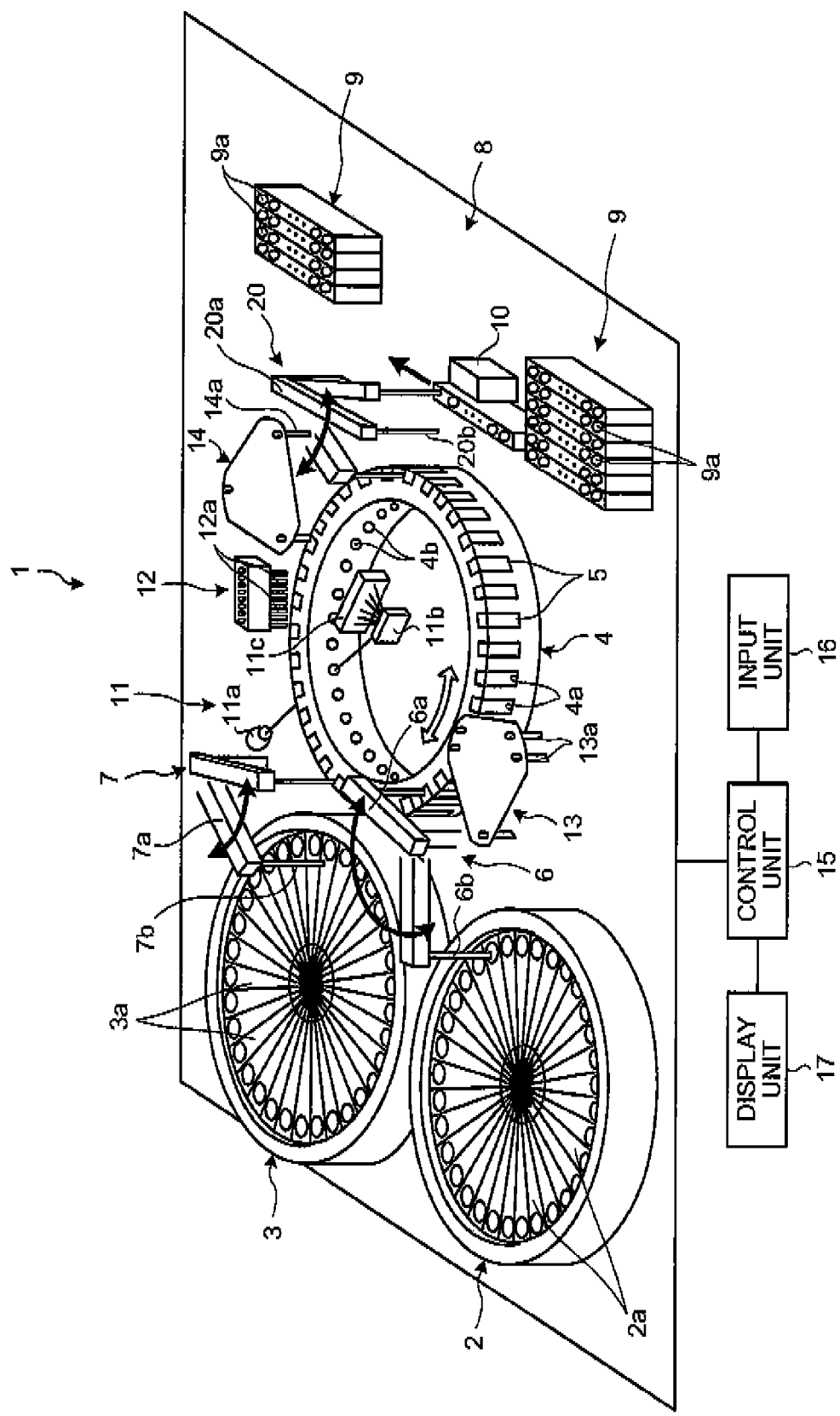
FIG. 1 shows a schematic configuration of an automatic analyzer of the present invention.
Figure 2:
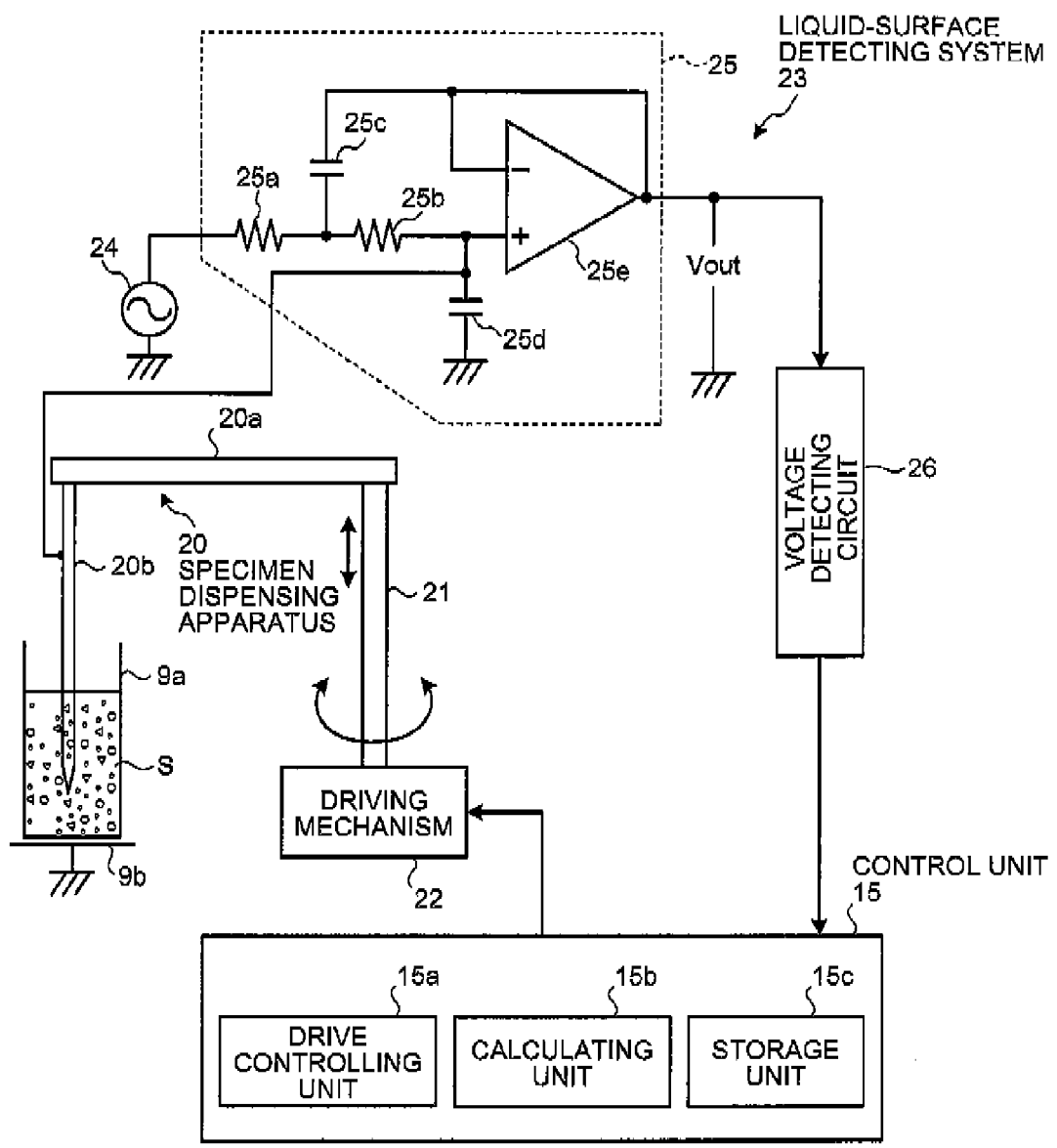
FIG. 2 shows a block diagram of a schematic configuration of a specimen dispensing apparatus used in the automatic analyzer shown in FIG. 1.

Exemplary embodiments according to an automatic analyzer of the present invention and a dispensing method thereof are described in detail with reference to accompanying drawings. FIG. 1 shows a schematic configuration of the automatic analyzer according to the present invention. FIG. 2 shows a block diagram of a schematic configuration of a specimen dispensing apparatus used in the automatic analyzer shown in FIG. 1.

An automatic analyzer 1 is an apparatus which automatically analyzes a specimen such as blood and urine containing components of blood cells. As shown in FIG. 1, the automatic analyzer 1 includes reagent tables 2 and 3, a cuvette wheel 4, a specimen-vessel transferring system 8, an analyzing optical system 11, a cleaning system 12, a first stirring apparatus 13, a second stirring apparatus 14, a control unit 15, and a specimen dispensing apparatus 20.

As shown in FIG. 1, on the reagent tables 2 and 3, plural reagent vessels 2a for first reagents and plural reagent vessels 3a for second reagents are arranged along a circumferential direction, respectively. The reagent tables 2 and 3 are revolved by a driving unit to transfer the reagent vessels 2a and 3a in the circumferential direction. The reagent vessels 2a and 3a are filled with reagents and pretreatment liquid which hemolyzes the component of blood cells for analysis items, respectively. An information recording medium (not shown) in which information such as type, lot, and expiration date of the contained reagent is written is appended to an outer surface of the reagent vessels 2a and 3a. A reading device which reads out reagent information written in the information recording medium appended to the reagent vessels 2a and 3a and outputs the information to the control unit 15 is arranged on outer circumferences of the reagent tables 2 and 3.

As shown in FIG. 1, in the cuvette wheel 4, plural reaction vessels 5 are arranged along a circumferential direction. The cuvette wheel 4 is revolved in a direction along the arrow by a driving unit different from the driving unit of the reagent tables 2 and 3 to move the reaction vessels in the circumferential direction. The cuvette wheel 4 is arranged between a light source 11a and a spectroscopic unit 11b. The cuvette wheel 4 includes holders 4a each holding the reaction vessel 5, and optical paths 4b each having circular openings from which light flux emitted from the light source 11a enters the spectroscopic unit 11b. The holders 4a are arranged on an outer circumference of the cuvette wheel 4 in the circumferential direction at predetermined intervals, and the optical paths 4b extending in a radial direction are arranged on a side of an inner circumference.

The reaction vessel 5 is a rectangular cylindrical vessel, so called cuvette, made of an optically transparent material such as glass including heat-resistant glass, cyclic olefin, and polystyrene, through which 80% or more of analysis light emitted from the analyzing optical system 11 is transmitted. The reagent is dispensed into the reaction vessel 5 by the reagent dispensing apparatuses 6 and 7 arranged in the vicinity from the reagent vessels 2a and 3a on the reagent tables 2 and 3. The reagent dispensing apparatuses 6 and 7 include arms 6a and 7a which are revolved in a horizontal surface and moved downward or upward in the vertical direction, and dispensing probes 6b, 7b which dispense the reagent. The reagent dispensing apparatuses 6 and 7 have a cleaning unit which cleans the dispensing probes 6b and 7b with cleaning water.

As shown in FIG. 1, the specimen-vessel transferring system 8 transfers plural arranged racks 9 in a direction along the arrow one by one through a stepping operation. The rack 9 holds plural specimen vessels 9a containing the specimen. A recording medium such as a bar code, in which specimen information of the contained specimen and shape information of the vessel are written, is appended to the specimen-vessel 9a. Every time the stepping operation of the rack 9 transferred by the specimen-vessel transferring system 8 is stopped, the specimen dispensing apparatus 20 dispenses the specimen into each of the reaction vessels 5. The shape information of the vessel written in the recording medium includes a type of the vessel, and further a thickness of a bottom wall of the vessel determined by the type of the vessel. Alternatively, to acquire the shape of the specimen vessel 9a, a shape detector which detects the shape based on an outer appearance of the specimen vessel 9a may be arranged in a transfer path of the rack 9 transferred by the specimen-vessel transferring system 8 so that the outer appearance of the specimen vessel 9a can be mechanically detected by the shape detector.

As shown in FIG. 1, the specimen-vessel transferring system 8 includes, as an information acquiring unit, a reading device 10 which reads out the recording medium appended to the specimen vessel 9a held in the rack 9, and outputs the read specimen information and shape information to the control unit 15. An electrode plate 9h (see FIG. 2) from which the liquid-surface detecting system (liquid level sensor) 23 can detect the liquid surface of the specimen contained in the specimen vessel 9a is provided on the rack 9.

The analyzing optical system 11 emits analysis light which transmits through a liquid sample in the reaction vessel in which the reagent and the specimen are reacted, and thus to analyze the liquid sample. As shown in FIG. 1, the analyzing optical system 11 includes the light source 11a, the spectroscopic unit 11b, and the light receiving unit 11c. The analysis light emitted from the light source 11a transmits through the liquid sample in the reaction vessel 5 to be received by the light receiving unit 11c arranged at an opposing position to the spectroscopic unit 11b. The light receiving unit 11c is connected with the control unit 15.

After the liquid sample in the reaction vessel 5 is sucked in and discharged by the nozzle 12a, the cleaning system 12 repeatedly discharges and sucks back in cleaning liquid such as detergent and cleaning water into the reaction vessel 5 to clean the reaction vessel 5 in which the analysis has been performed by the analyzing optical system 11.

The first stirring apparatus 13 and the second stirring apparatus 14 stir the dispensed specimen and the dispensed reagent with stir bars 13a and 14a, respectively, so that they are reacted.

The control unit 15 is realized by a microcomputer or the like. The control unit 15 is connected with the reagent tables 2 and 3, the reagent dispensing apparatuses 6 and 7, the specimen-vessel transferring system 8, the analyzing optical system 11, the cleaning system 12, the stirring apparatuses 13 and 14, an input unit 16, a display unit 17, the specimen dispensing apparatus 20, and the like. The control unit 15 controls operations of each of the components. As shown in FIG. 2, the control unit 15 includes a drive controlling unit 15a, a calculating unit 15b, and a storage unit 15c.

The drive controlling unit 15a controls operations of each of the components of the automatic analyzer 1, and controls a driving mechanism 22 so that a distal end of a dispensing probe 20b and the liquid surface of the liquid contained in the specimen vessel 9a are moved relatively to each other in the vertical direction. Specifically, in dispensing the specimen including the precipitated substance, for example, in dispensing whole blood to analyze components of red blood cells HbA1C, the drive controlling unit 15a controls the driving mechanism 22 so that the specimen is sucked in from plural different positions along the vertical direction based on liquid-surface information detected by a voltage detecting circuit 26. The drive controlling unit 15a stores therein a sucking condition of the specimen which is input from the input unit 16, and controls the driving mechanism 22 based on the sucking condition. The drive controlling unit 15a specifies the type of the specimen vessel 9a based on the shape information of the specimen vessel 9a acquired by the reading device 10 or the shape detector, and determines, based on the thickness of the bottom wall which is determined by the type, the lower limit position to which the dispensing probe can be lowered, i.e., a position of the insertion depth 100% for the dispensing probe to suck in the specimen, and further outputs the position information of the insertion depth 100% of the specimen vessel 9a to the storage unit 15c. When the lot of the reagent is different or when the reagent is out of the expiration date, or the like based on the information read out from the information recording medium appended to the reagent vessels 2a and 3a, the drive controlling unit 15a controls the automatic analyzer 1 to stop the analysis operation, or warns an operator.

Figure 3:
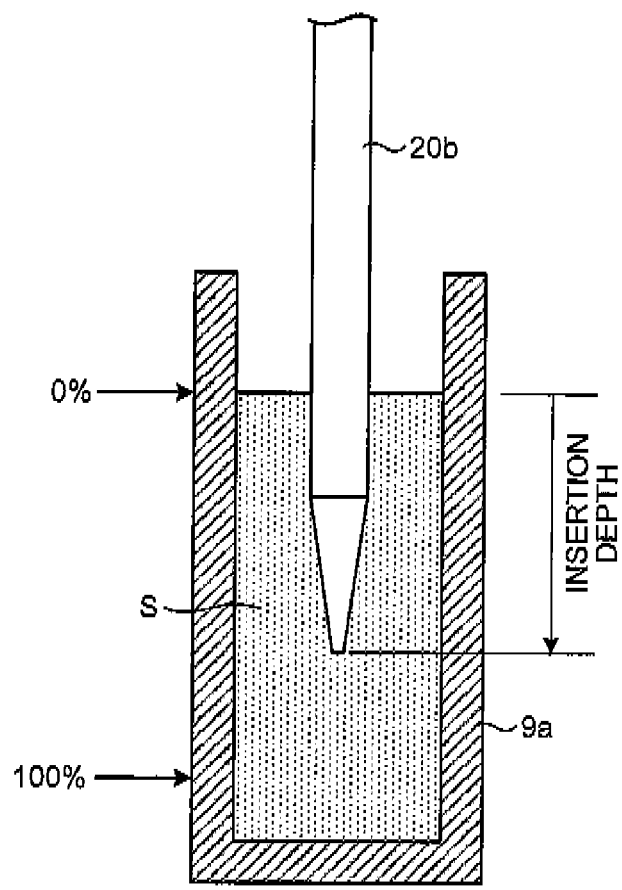
FIG. 3 shows an illustration of an insertion depth of a dispensing probe inserted into a specimen.

The insertion depth of the dispensing probe represents the insertion amount from the liquid surface of the specimen below the distal end of the dispensing probe 20b into the specimen by percentage. As shown in FIG. 3, the position of the liquid surface of the specimen S is set at 0%, and the lower limit position of the dispensing probe 20b in the vertical direction is set at 100%. The bottom, wall of the specimen vessel 9a in FIG. 3 is a plane surface for convenience of the description. The bottom wall of the specimen vessel 9a may be a curved surface, and also in this case, a position to which the dispensing probe 20b can be lowered is determined as the lower-limit position based on the thickness of the bottom wall.

The calculating unit 15b calculates absorbance of the liquid sample in each reaction vessel for each wavelength based on a light amount signal input from the light-receiving unit 11c to analyze constituent concentration of the specimen. The storage unit 15c stores therein calibration data, an analysis result, and the like needed for the analysis operation of the automatic analyzer 1 which can be used in various analysis modes, or the calculation of the absorbance. The storage unit 15c stores therein the location information of the insertion depth 100% input from the drive controlling unit 15a for each of the specimen vessels 9a.

The input unit 16 performs an input operation for inputting analysis items, procedure for dispensing the specimen including the precipitated substance, and the like. The input unit 16 is, for example, realized by a keyboard, a mouse, and the like. The display unit 17 displays an analysis content, the analysis result, the warning, and the like. The display unit 17 is realized by a display panel and the like. Further, the automatic analyzer 1 includes an output unit which prints out the analysis result in a form of a table or the like.

As shown in FIG. 2, in the specimen dispensing apparatus 20, a dispensing probe 20b which dispenses the specimen is provided on an arm 20a which is driven by the driving mechanism 22. The arm 20a is supported by a supporting column 21 which is raised and lowered, and revolved by the driving mechanism 22. The dispensing probe 20b is a component of the liquid-surface detecting system 23, and, for example, is made of a conductive material such as stainless steel. In sucking in the component of blood cells, the dispensing probe 20b moving upward may not be able to suck in the component of blood cells due to a high concentration. Thus, the dispensing probe 20b is preferably moved downward to suck in the component of blood cells. Inner and cuter surfaces of the dispensing probe 20b to which the specimen has been attached are cleaned at a cleaning tank (not shown) always after the specimen is dispensed.

The liquid-surface detecting system 23 detects the liquid surface of the specimen in the specimen vessel 9a, and includes an oscillating circuit 24, a differentiating circuit 25, and a voltage detecting circuit 26.

The oscillating circuit 24 oscillates and transmits an alternating-current signal to be input into the differentiating circuit 25. As shown in FIG. 2, the differentiating circuit 25 includes resistors 25a and 25b, capacitors 25c and 25d, and an operational amplifier 25e. The differentiating circuit 25 is configured such that input sensitivity becomes high depending on the frequency of the alternating signal transmitted from the oscillating circuit 24 which is oscillating. A positive input terminal of the differentiating circuit 25 is connected with the dispensing probe 20b via a lead wire 23a. The voltage detecting circuit 26 is connected with an output terminal of the differentiating circuit 25 to detect output voltage $V_{out}$ of the differentiating circuit 25. Based on the detected value, the voltage detecting circuit 26 detects the liquid-surface position of the specimen contained in the specimen vessel 9a, the liquid-surface position touching the lower end of the dispensing probe 20b. The detected liquid-surface position is output to the drive controlling unit 15a as a liquid-surface-position signal. Then, the drive controlling unit 15a determines the liquid-surface position as the position of the insertion depth 0% of the dispensing probe 20b for dispensing the specimen.

The differentiating circuit 25 is configured such that the input sensitivity becomes high depending on the frequency of the oscillating circuit 24 due to capacitance when the dispensing probe 20b does not touch the liquid surface of the liquid. With the capacitance when the dispensing probe 20b touches the liquid surface, the input sensitivity of the differentiating circuit 25 is lowered. Thus, the voltage detecting circuit 26 detects the liquid surface based on the change in the output voltage $V_{out}$. The positive input terminal of the differentiating circuit 25, the oscillating circuit 24, the electrode plate 9b arranged on the rack 9 are connected with each other via ground lines.

In the automatic analyzer 1 configured as above, the reagent dispensing apparatus 6 sequentially dispenses the first reagent from the reagent vessel 2a into the plural reaction vessels 5 transferred along the circumferential direction by the revolving cuvette wheel 4. Then, the specimen dispensing apparatus 20 sequentially dispenses the specimen from the plural specimen vessels 9a held in the rack 9 into the reaction vessels into which the first reagent has been dispensed. The first stirring apparatus 13 stirs the liquid in the reaction vessel 5 into which the specimen has been dispensed every time the cuvette wheel stops revolving so that the first reagent and the specimen are reacted. The reagent dispensing apparatus 7 dispenses the second reagent from the reagent vessel 3a into the reaction vessel in which the reagent and the specimen have been stirred. Then, the liquid in the reaction vessels are stirred by the second stirring apparatus 14 to promote the reaction further when the cuvette wheel stops revolving. One the first reagent and the second reagent may be dispensed depending on the specimen to be analyzed.

The cuvette wheel 4 resumes revolving, and transfers the reaction vessels 5 relative to the light source 11a, and the reaction vessels 5 pass through the analyzing optical system 11. The light receiving unit 11c outputs the optical signal to the control unit 15. The control unit 15 obtains the absorbance of the liquid sample in the each reaction vessel 5 for each wavelength based on the light amount signal which is input for each wavelength from the light receiving unit 11c. Then the constituent concentration and the like of the specimen are analyzed. The control unit 15 stores the analysis result of the constituent concentration and the like of the analyzed specimen, and displays the analysis result on the display unit 17. The reaction vessel 5 which has undergone the analysis is cleaned by the cleaning system 12, and used for the analysis of the specimen again.

When the specimen dispensing apparatus 20 dispenses the specimen including the precipitated substance, e.g., the whole blood from the specimen vessel 9a held in the rack 9, the drive controlling unit 15a controls the driving mechanism 22 to stop the dispensing probe 20b at the plural different positions along the vertical direction. At each of the stopped positions, the dispensing probe 20b sequentially sucks in the whole blood. The dispensing probe 20b discharges the whole blood into the reaction vessel 5. A dispensing method with the dispensing probe performed by the control unit 15 is described with reference to the flowchart shown in FIG. 4.

To prepare for the dispense of the specimen, the operator sets the rack 9 holding the specimen vessels 9a on the specimen-vessel transferring system 8, and inputs the sucking condition on which the dispensing probe 20b sucks in the whole blood sample via the input unit 16. The sucking condition is, for example, that the dispensing probe 20b is stopped at three positions of the insertion depths 0%, 40%, and 100% to intermittently suck in the whole blood sample. After that, the automatic analyzer 1 starts dispensing the whole blood under the control by the control unit 15.

The insertion depth 100% is previously set at the position where the dispensing probe 20b does not touch the bottom of the specimen vessel 9a. When plural types of specimen vessels are used, the insertion depth 100% is set for each type of the specimen vessels 9a. The type of the specimen vessel 9a is acquired by checking the shape of the vessel or reading the recording medium such as the bar code appended to the specimen vessel 9a so that the position of the insertion depth 100% can be changed depending on the type of the specimen vessel 9a.

Figure 4:
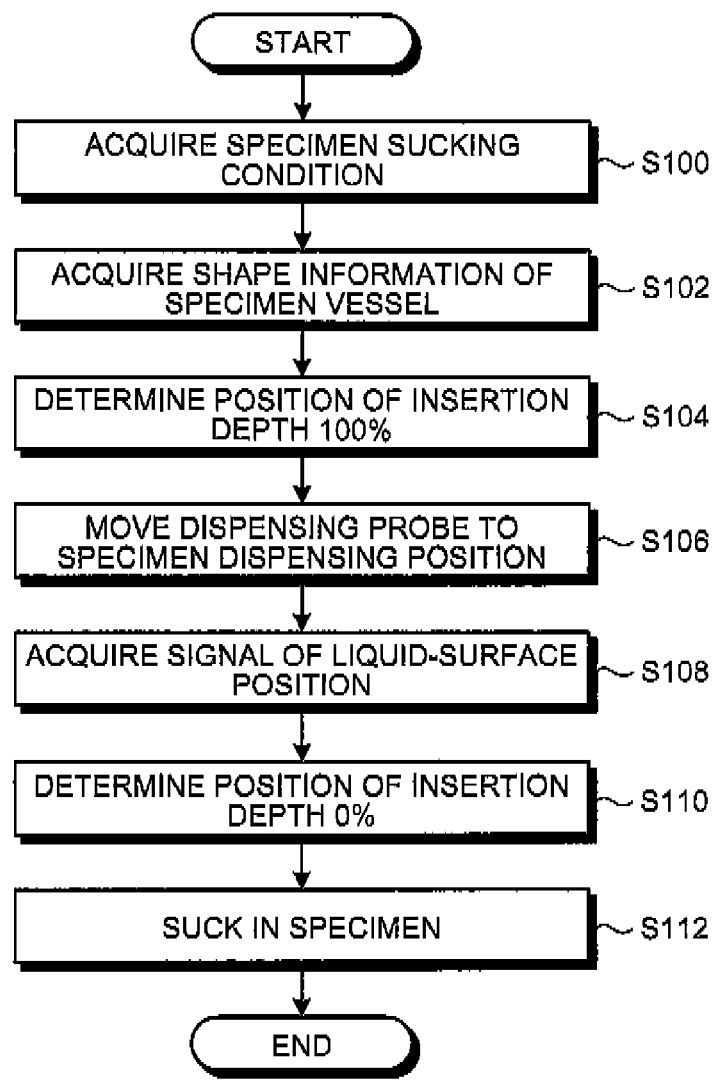
FIG. 4 shows a flow chart explaining a dispensing method of the present invention.

As shown in FIG. 4, in dispensing the whole blood sample, to begin with, the control unit acquires the sucking condition of the specimen which is input via the input unit 16 from the drive controlling unit 15a (Step S100). After that, the control unit 15 acquires the shape information of the specimen vessel 9a which is output from the reading device 10 (Step S102). The control unit 15 determines the position of the insertion depth 100% of the dispensing probe 20b based on the type of the specimen vessel 9a which is specified based on the acquired shape information (Step S104).

The control unit 15 moves the dispensing probe 20b to the specimen dispense position (Step S106). The control unit 15 lowers the dispensing probe 20b according to the sucking condition for intermittently sucking in the specimen, and obtains the liquid-surface-position signal output from the liquid-surface detecting system 23 (Step S108). The acquisition of the liquid-surface-position signal is equivalent to detection of the liquid surface. After that, the control unit 15 determines the position of the insertion depth 0% of the dispensing probe 20b based on the acquired liquid-surface-position signal (Step S110).

The control unit 15 controls the dispensing probe 20b to suck in the specimen (Step S112). The dispensing method is completed as above. When the amount of the component of blood cells to be sucked in is set at 6 μL, and the positions for sucking in the specimen are set at the insertion depths 0, 40, and 100%, the automatic analyzer 1 sucks in 2 μL of the component of blood cells at each of the stopped positions of the insertion depths 0, 40, and 100%.

Figure 5:
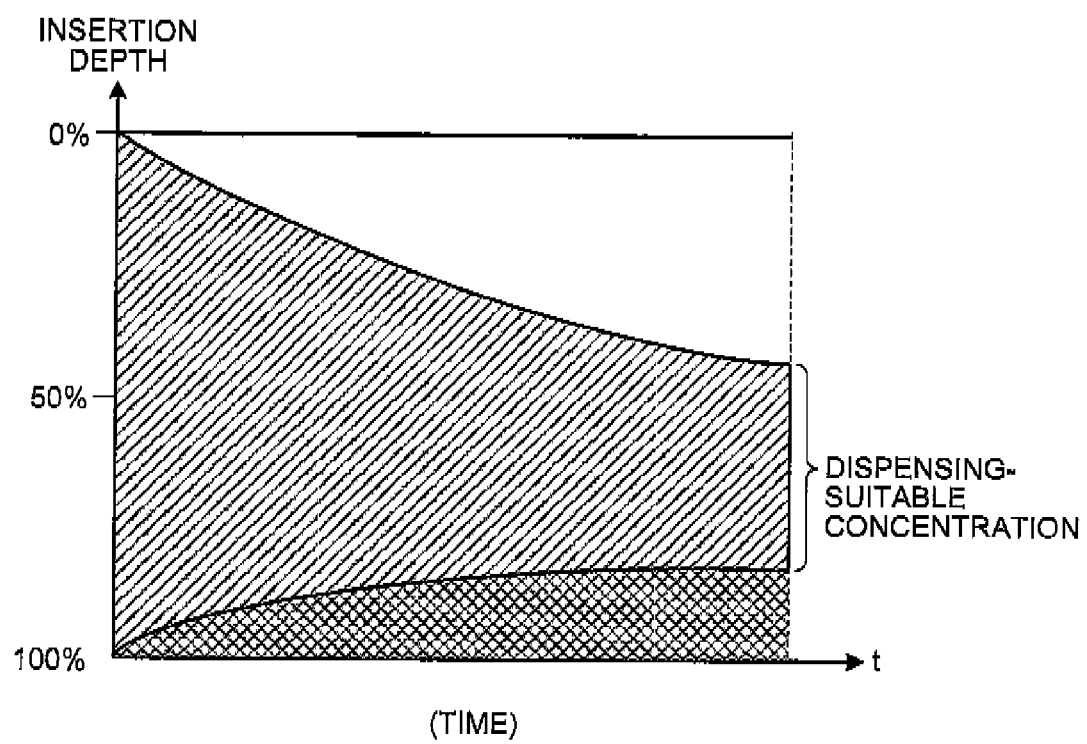
FIG. 5 shows a schematic diagram of time change of a dispense-suitable concentration of components of blood cells in a whole-blood sample to the insertion depth due to precipitation of the blood cells.

In the whole blood sample, the component of the blood cells is precipitated as time goes. The component of the blood cells is dilute in an upper layer, and dense in a lower layer. The range of the dispense-suitable concentration C in the whole blood sample changes over time as shown by a schematic diagram in FIG. 5. Thus, the component of blood cells is sucked in from the whole blood sample by 2 μL at each of the stopped positions of the insertion depths 0, 40, and 100%. When the component of blood cells is sucked in as above, the total amount 6 μL of component of blood cells has averaged concentration which is an average of the conditions at each of the insertion depths.

The sucking position is not limited to the above. For example, the insertion depths 0 and 100%, or the insertion depths 20, 50, 70% may be set. Further, a sucking amount at each of the sucking positions may be different.

After the dispensing probe 20b sucks in the specimen, the control unit 15 controls the driving mechanism 22 to move the dispensing probe 20b to the dispense position of the reaction vessel 5, and discharges the sucked specimen into the reaction vessel 5. After that, the control unit 15 controls the driving mechanism 22 to move the dispensing probe 20b to the cleaning tank to wash the dispensing probe 20b which has discharged the specimen. The control unit 15 moves on to the operation for dispensing the new whole blood sample from the following specimen vessel 9a held in the rack 9.

The automatic analyzer 1 according to the present invention dispenses the whole blood sample from the specimen vessel 9a held in the rack 9 as above into the reaction vessel 5. In dispensing the sample, the component of blood cells is sucked in at the plural different positions along the vertical direction of the whole blood sample. Thus, according to the dispensing method of the present invention, fluctuation in the concentration of the whole blood sample is minimized, and the component of the blood cells which has substantially the same concentration as the concentration when the whole blood is mixed can be easily dispensed from the specimen vessel 9a regardless of how the component of blood cells is precipitated.

In the embodiment described above, the sucking condition of the specimen is set for the dispensing probe 20b to intermittently suck in the specimen, and at Step S112, where the dispensing probe 20b sucks in the specimen, the dispensing probe 20b is stopped at plural different positions along the vertical direction to sequentially suck in the component of blood cells from the whole blood sample at each of the stopped positions. The sucking condition of the specimen, however, may be set for the dispensing probe 20b to successively suck in the specimen, and at Step S112, where the dispensing probe 20b sucks in the specimen, the dispensing probe 20b may successively suck in the component of blood cells from the whole blood sample while moving downward from the insertion depth 0% to the insertion depth 100%. In this case, the automatic analyzer 1 further provides advantage that the control unit 15 can control the driving mechanism 22 more easily to operate the specimen dispensing apparatus 20.

In the embodiment described above, the specimen including the precipitated substance is dispensed. The present invention, however, is not limited to the dispensing of the specimen as long as the liquid including the precipitated substance is dispensed. For example, the present invention may be applied to a case where the reagent including the precipitated substance is dispensed.

When the specimen vessels 9a are identical and contain the same amount of the specimen, the specimen dispensing apparatus 20 may not include the liquid-surface detecting system 23, and the shape detector and the reading device 10 for acquiring the shape of the specimen vessel 9a may not be included.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A dispensing method for dispensing a liquid including a precipitated substance contained in a vessel with a dispensing probe, the dispensing method, comprising:
   receiving user input of plural positions which differ from each other in a vertical direction,
   determining a shape of the vessel,
   determining a type of the vessel based on the determined shape of the vessel, where each type of vessel has a bottom wall of a known thickness,
   determining a lower-limit position of the dispensing probe, based on the thickness of the bottom wall,
   determining a liquid surface of the liquid in the vessel using a liquid level sensor,
   sucking in the liquid into the dispensing probe from said plural positions, said plural positions ranging from said lower-limit position to said liquid surface, and
   dispensing the liquid from the dispensing probe
   wherein the shape of the vessel is determined (i) by obtaining shape information associated with the vessel from a recording medium attached to the vessel, or (ii) by using a shape detector which detects the outer appearance of the vessel.

2. The dispensing method according to claim 1, wherein in the wherein during the sucking, the dispensing probe stops at the plural positions which differ from each other along the vertical direction to suck in the liquid.

3. The dispensing method according to claim 1, the liquid is sucked in while the dispensing probe is moved in the vertical direction.

4. The dispensing method according to claim 3, wherein the liquid is sucked in while the dispensing probe is moved vertically in an up-to-down direction.

5. The dispensing method according to claim 1, wherein the shape of the vessel is determined by a reader which reads the recording medium attached to the vessel.

6. The dispensing method according to claim 1, wherein the shape of the vessel is determined by the shape detector.

* * * * *